United States Patent [19]

Okinoshima et al.

[11] Patent Number: 5,059,705
[45] Date of Patent: Oct. 22, 1991

[54] BUTADIENYL GROUP-CONTAINING SILOXANE COMPOUNDS AND METHOD OF PRODUCING THE SAME

[75] Inventors: Hiroshige Okinoshima, Annaka; Hiroshi Kanbara, Takasaki, both of Japan

[73] Assignee: Shin-Etsu Chemical Co., Ltd., Tokyo, Japan

[21] Appl. No.: 662,038

[22] Filed: Feb. 28, 1991

[30] Foreign Application Priority Data

Feb. 28, 1990 [JP] Japan .................... 2-48318

[51] Int. Cl.$^5$ .............................. C07F 7/08
[52] U.S. Cl. ........................ 556/453; 556/454
[58] Field of Search ................. 556/453, 454

[56] References Cited

U.S. PATENT DOCUMENTS

| | | | |
|---|---|---|---|
| 3,269,983 | 8/1966 | Holbrook | 556/454 X |
| 4,611,042 | 9/1986 | Rivers-Farrell et al. | 556/453 X |
| 4,683,320 | 7/1987 | Hida et al. | 556/453 |
| 4,874,881 | 10/1989 | Suzuki et al. | 556/453 |
| 4,876,373 | 10/1989 | Okawa et al. | 556/453 |

*Primary Examiner*—Paul F. Shaver
*Attorney, Agent, or Firm*—Nixon & Vanderhye

[57] ABSTRACT

Siloxane compounds having the following formula [1]:

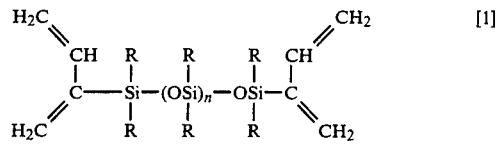

wherein each R is a substituted or unsubstituted monovalent hydrocarbon group having from 1 to 10 carbon atoms, and n is an integer of from 0 to 100. The compounds are extremely high in reactivity and, therefore, useful as an intermediate or modifying agent in the synthesis of silicone resins and other various organic resins.

10 Claims, 2 Drawing Sheets

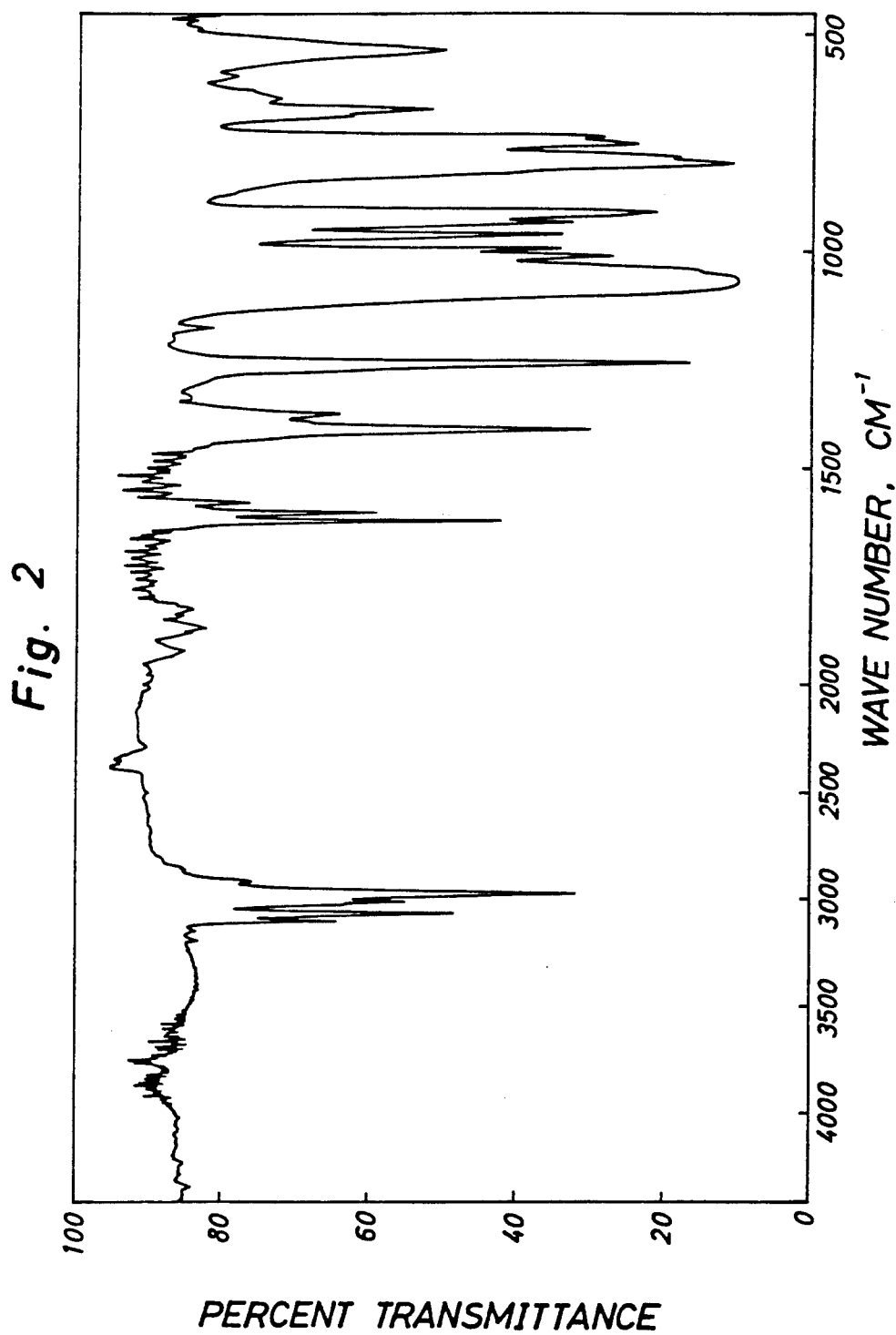

BUTADIENYL GROUP-CONTAINING SILOXANE COMPOUNDS AND METHOD OF PRODUCING THE SAME

BACKGROUND OF THE INVENTION

1. Field of the Invention

This invention relates to novel siloxane compounds comprising a 1,3-butadienyl group, and to a method of producing the same.

2. Description of the Prior Art

Silane compounds in which two [2-(1,3-butadienyl)] groups are bonded to a silicon atom, namely, bis-substituted 1,3-butadienylsilane derivatives have been known (Japanese Pre-examination Patent Publication (KOKAI) No. 61-205286 (1986)).

However, siloxane compounds in which a [2-(1,3-butadienyl)] group is bonded to each of silicon atoms at both terminal ends of the siloxane skeleton have not hitherto been known, although such siloxane compounds have high reactivity and are considered to be useful as an intermediate in the production of silicone resins and other various organic resins.

SUMMARY OF THE INVENTION

Accordingly, it is an object of this invention to provide a siloxane compound in which a [2-(1,3-butadienyl)] group is bonded to each of silicon atoms at both terminal ends of the siloxane skeleton, and a method of producing the same.

According to this invention, there is provided a butadienyl group-containing siloxane compound having the following formula [1]:

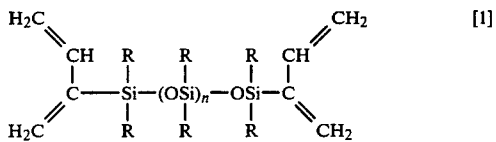

wherein each R is a substituted or unsubstituted monovalent hydrocarbon group having from 1 to 10 carbon atoms, the R groups may be the same or different, and n is an integer of from 0 to 100.

The novel siloxane compounds of this invention, in view of their molecular structure comprising the highly reactive butadienyl group bonded to each end of the siloxane chain, are expected to be used widely as an intermediate or modifying agent in the synthesis of silicone resins and other various organic resins. In particular, those having an alkenyl group bonded to the siloxane skeleton can introduce various functional groups therein and can undergo crosslinking reaction; therefore, they are expected to be applied extensively in syntheses of a variety of silicone compounds.

BRIEF DESCRIPTION OF THE DRAWINGS

FIG. 2 is a graph showing an infrared absorption spectrum of the compound obtained in Example 3.

DETAILED DESCRIPTION OF THE INVENTION

Butadienyl group-containing siloxane compound

Figure 1:
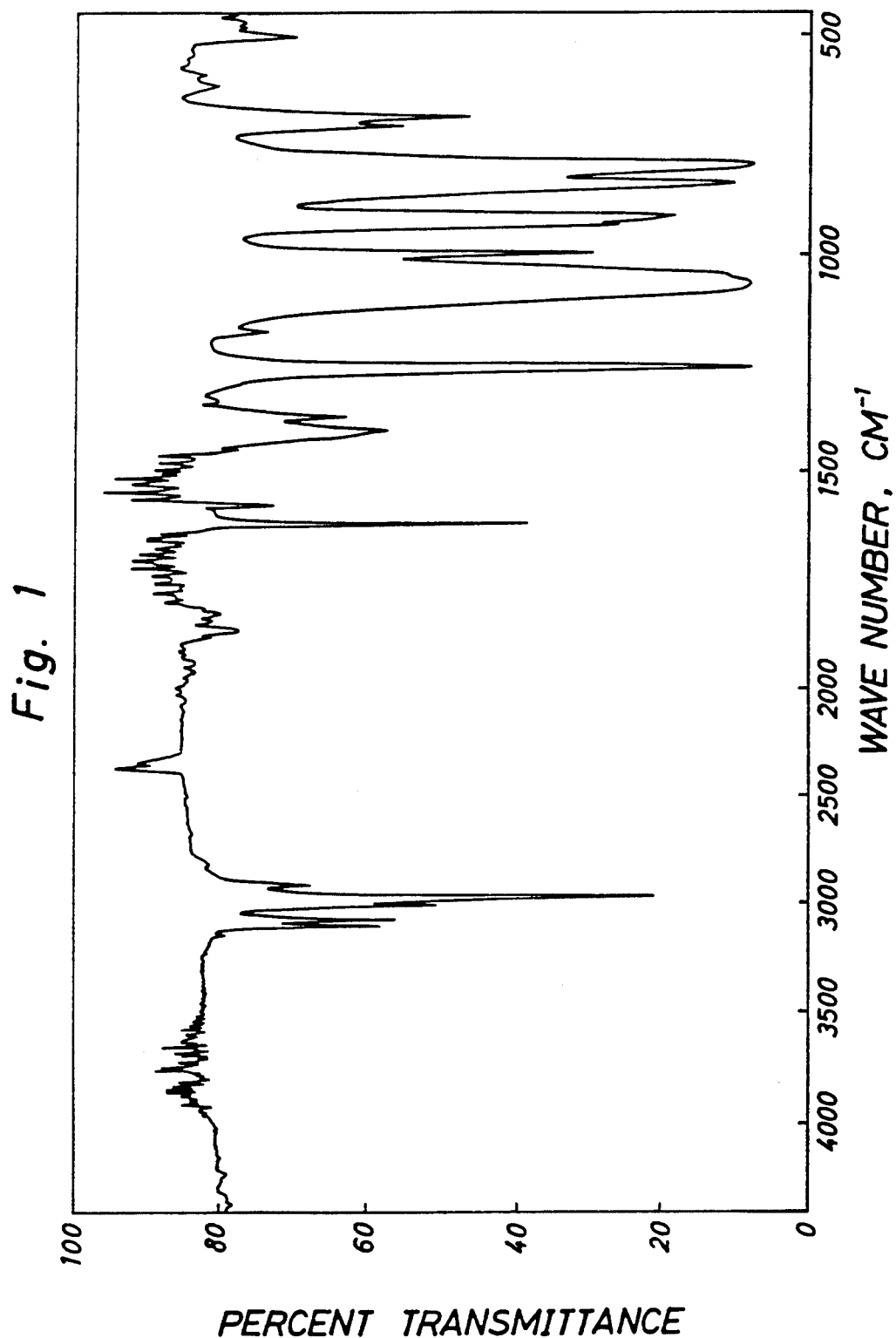
FIG. 1 is a graph showing an infrared absorption spectrum of the siloxane compound synthesized in Example 1.

The novel siloxane compounds according to this invention have the aforementioned formula [1], namely:

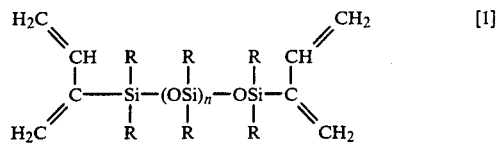

As is clear from the formula, the siloxane compounds of this invention have a distinguishing characteristic in that the [2-(1,3-butadienyl)] group, having a very high reactivity, is bonded to each of the two terminal silicon atoms of the siloxane chain.

In the formula [1], each R is a monovalent hydrocarbon group having from 1 to 10 carbon atoms, typical examples of which include lower alkyl groups, lower alkenyl groups, aryl groups, etc., and in which some or all of the carbon-bonded hydrogen atoms may be replaced by halogen atoms or the like. More specifically, the lower alkyl groups include, for example, methyl, ethyl, propyl and butyl groups and groups derived from these groups by substitution of halogen atoms for some or all of the hydrogen atoms in these groups. The lower alkenyl groups include, for example, vinyl, allyl and butenyl groups and groups derived from these groups by substitution of halogen atoms for some or all of the hydrogen atoms in these groups. The aryl groups include, for example, phenyl, tolyl and naphthyl groups and groups derived from these groups by substitution of halogen atoms for some or all of the hydrogen atoms in these groups. The plurality of R groups may all be the same or may be different from each other.

Further, n is an integer of from 0 to 100.

In this invention, typical examples of the butadienyl group-containing siloxane compound are those having the following formula [2]:

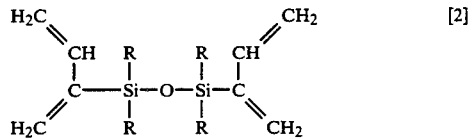

wherein R is as defined above.

Typical exemplars of R in the formula [2] include $C_1$–$C_4$ lower alkyl groups such as methyl, ethyl, propyl and butyl, $C_1$–$C_4$ lower alkenyl groups such as vinyl, allyl and butenyl, $C_6$–$C_{15}$ aryl groups such as phenyl, tolyl and naphtyl, and corresponding substituted hydrocarbon groups in which part or all of the hydrogen atoms of the above hydrocarbon groups have been substituted by a halogen atom such as fluorine, chlorine or bromine.

More specific examples of the compound of formula [2] include 1,1,3,3-tetramethyl-1,3-bis[2-(1,3-butadienyl)]disiloxane, 1,3-dimethyl-1,3-divinyl-1,3-bis-[2-(1,3-butadienyl)]disiloxane, and 1,1,3,3-tetravinyl-1,3-bis[2-(1,3-butadienyl)]disiloxane.

Production method

The butadienyl group-containing siloxane compounds having the formula [1] can be produced easily by the following exemplary methods (1) and (2).

Method (1)

The compounds of the formula [1] can be obtained by a method comprising the step of reacting:

(a) a 1,3-butadien-2-yl magnesium halide having the following formula [3]:

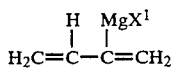

wherein $X^1$ is a halogen atom, with (b) a siloxane compound having the following formula [4]:

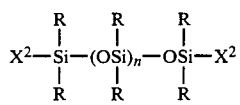

wherein each $X^2$ is a halogen atom or an alkoxy group, the two $X^2$ groups may be the same or different from each other, and R and n are as defined above.

The Grignard reagent to be used in this production method is a 1,3-butadien-2-yl magnesium halide having the above formula [3]. The halogen atom may be any of chlorine, bromine and iodine atoms.

The Grignard reagent can be produced easily by mixing a 2-halo-1,3-butadiene and metallic magnesium in an ether solvent such as tetrahydrofuran, dioxane and diethyl ether, according to a method which is known per se, for example, the method described in J. Org. Chem., 44, 4788 (1979).

The siloxane compound to be reacted with the above Grignard reagent is a halo- or alkoxy-substituted siloxane compound having the above formula [4], with the siloxane skeleton corresponding to the desired butadienyl group-containing siloxane compound of the formula [1].

In the formula [4], the halogen atom as the group $X^2$ may be any of chlorine, bromine and iodine atoms, whereas the alkoxy groups usable as the group $X^2$ include methoxy, ethoxy, methoxy-substituted ethoxy, ethoxy-substituted ethoxy, propoxy and butoxy groups, and groups derived from these groups by substitution of halogen atoms for some or all of the carbon-bonded hydrogen atoms in these groups. Furthermore, the two $X^2$ groups may be the same or different from each other.

Such a halo- or alkoxy-substituted siloxane compound can be produced by the methods which are known per se.

The reaction of the Grignard reagent with the siloxane compound can be carried out by cooling the Grignard reagent, prepared in a solvent which does not hinder the reaction, such as tetrahydrofuran, to or below room temperature, and adding the siloxane compound dropwise thereto in the presence of an inert gas. The reaction can also be carried out in a manner reverse to the above, namely, by diluting the siloxane compound with a solvent, and adding the Grignard reagent, previously prepared, dropwise thereto with cooling and stirring. The reaction is carried out at a temperature of generally from −50° C. to the boiling point of the solvent (ordinarily, from −50 to 100° C.), preferably from 0° to 30° C. If the reaction temperature is too low, the reaction proceeds so slowly as to be impractical, whereas too high a reaction temperature may cause side reactions. The reaction is performed for a period of generally from 5 minutes to 6 hours, preferably from 30 minutes to 3 hours.

The ratio of the amount of the Grignard reagent used to the amount of the siloxane compound used is in the range from 1:0.1 to 1:2, preferably from 1:0.2 to 1:1, on a molar basis.

The amount of the solvent to be used, or the degree of dilution of the reaction mixture, may be determined taking the heat of reaction, volumetric efficiency, etc. into account.

The reaction between the Grignard reagent and the siloxane compound is ordinarily carried out in an inert gas atmosphere, as mentioned above. The inert gases which can be used include, for example, argon, helium, nitrogen, etc., which may be used either singly or in combination of two or more, and of which a nitrogen gas is preferred from an economical point of view.

By the reaction as above, the butadienyl group-containing siloxane compound of this invention having the formula [1] can be produced.

Method (2)

Of the butadienyl group-containing siloxane compounds according to this invention, those having the aforementioned formula [2], namely the formula:

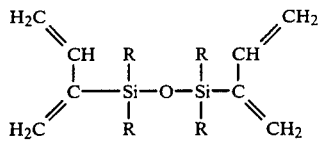

wherein R is as defined above, can be also obtained by a method which comprises the step of subjecting a butadienyl group-containing silane having the formula [5]:

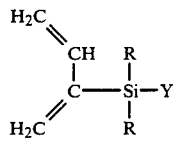

wherein Y is a hydrolyzable atom or group, and R is as defined above, to a hydrolysis and condensation reaction.

In the formula [5], R is as defined above, and typical examples thereof include $C_1$–$C_4$ lower alkyl groups such as methyl, ethyl, propyl and butyl, $C_1$–$C_4$ lower alkenyl groups such as vinyl, allyl and butenyl, $C_6$–$C_{15}$ aryl groups such as phenyl, tolyl and naphtyl, and corresponding substituted hydrocarbon groups in which part or all of the hydrogen atoms of the above hydrocarbon groups have been substituted by a halogen atom such as fluorine, chlorine or bromine. The hydrolyzable atom or group Y include, for example, halogen atoms selected from the group consisting of chlorine, bromine and iodine atoms; alkoxy groups such as methoxy, ethoxy, methoxy-substituted ethoxy, ethoxy-containing ethoxy, propoxy and butoxy groups; substituted alkoxy groups derived from the above alkoxy groups by substitution of halogen atoms, such as fluorine, chlorine and bromine atoms, for some or all of the carbon-bonded hydrogen atoms in these groups; and so on. Of these atoms and groups, preferred are halogen atoms and alkoxy groups.

The hydrolysis of the butadienyl group-containing silane having the formula [5] can be carried out by preparing an aqueous solution of an alkali compound such as sodium hydroxide, potassium hydroxide, sodium carbonate, etc. at room temperature, and adding dropwise thereto the butadienyl group-containing silane diluted with a solvent which does not hinder the hydrolysis, such as, for example, alkane solvents such as pentane, hexane and heptane, aromatic hydrocarbon solvents such as benzene, toluene and xylene, ether solvents such as tetrahydrofran, dioxane and diethylether, halogenated alkanes such as methylene chloride, chloroform and carbon tetrachloride. The hydrolysis can also be carried out in a manner reverse to the above, namely, by diluting the butadienyl group-containing silane with the solvent, and adding the aqueous alkali compound solution dropwise thereto.

By the process as above, the hydrolyzable atom or group Y in the silane of formula [5] is hydrolyzed, with the attendant conversion to the silanol group. The silanol group thus formed on one molecule of the hydrolyzate condenses immediately with the silanol group of another molecule, resulting in the formation of the intended compound of formula [2].

The hydrolysis and condensation reaction is carried out at a temperature of generally from 0° C. to the boiling point of the solvent (ordinarily, from 0° to 100° C.), preferably from 10° to 30° C. If the reaction temperature is too low, the reaction proceeds so slowly as to be impractical, whereas too high a reaction temperature may cause side reactions. The reaction is carried out for a period of generally from 30 minutes to 24 hours, typically from 2 to 12 hours. The molar ratio of the silane of formula [5] to the alkali compound, which are used in this method, is in the range from 1:0.5 to 1:10, preferably from 1:1 to 1:5. The amount of the solvent to be used, or the degree of dilution of the reaction mixture, may be determined taking the heat of reaction, volumetric efficiency, etc. into account. In the above hydrolysis reaction, the butadienyl group-containing silane may either consist of only one such silane or consist of two or more such silanes differing in the kind of the substituent R or Y in the above formula [5]. When two or more butadienyl-group containing silanes differing in the R groups are used, it is possible to produce a butadienyl group-containing siloxane having the aforementioned general formula [2] in which the different R groups are bonded to the two silicon atoms, respectively.

Besides, the silane compound of the formula [5], for use as a starting material in the above method (2), can be synthesized, for example, by reacting a silane having the general formula [6]:

[6]

wherein R and Y are as defined above, with a Grignard reagent having the aforementioned formula [3].

The reaction of the silane of formula [6] and the Grignard reagent of formula [3] can be carried out by cooling the Grignard reagent, prepared in a solvent which does not hinder the reaction, such as tetrahydrofuran, to or below room temperature, and adding the silane dropwise thereto in the presence of an inert gas. The reaction can also be carried out in a manner reverse to the above, namely, by diluting the silane with a solvent, and adding the Grignard reagent, previously prepared, dropwise thereto with cooling and stirring.

EXAMPLES

This invention will now be further illustrated by the following nonlimitative examples.

EXAMPLE 1

A 2-liter flask equipped with a reflux condenser, a thermometer, a stirrer and a dropping funnel was charged with 300 ml of a tetrahydrofuran solution of 1,3-butadien-2-yl magnesium chloride (330 mmol) under a stream of nitrogen. The contents of the flask was cooled to 0° C., and 16.7 g (82 mmol) of 1,1,3,3-tetramethyl-1,3-dichlorosiloxane as added dropwise thereto. Next, the reaction mixture was heated and aged for 1 hour under reflux of tetrahydrofuran. After the aging was over, the excess Grignard reagent in the reaction mixture was hydrolyzed by use of an aqueous solution of ammonium chloride. Then, the aqueous layer was extracted with n-hexane, and the organic layer thus obtained was distilled, to give 8.8 g of the objective compound (yield: 45%).

The compound was subjected to measurement of NMR, mass spectrum, IR absorption spectrum and elemental analysis. The results are given below.

It was confirmed by the measurement results that the compound obtained above is 1,1,3,3-tetramethyl-1,3bis-[2-(1,3-butadienyl)]disiloxane.

$^1$HNMR: CCl$_4$
δ (ppm)
0.37 (S, 12H, SiCH$_3$)

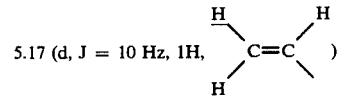
5.17 (d, J = 10 Hz, 1H, )

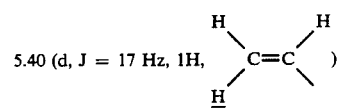
5.40 (d, J = 17 Hz, 1H, )

5.57, 5.80 (2d, J = 3 Hz, 2H, CH$_2$=C)
6.49 (dd, J = 10.17 Hz, 1H, CH=CH$_2$)
Mass spectrum:
238 (M$^+$), 223 (M$^+$ —CH$_3$)
IR absorption spectrum: shown in FIG. 1.

| (cm$^{-1}$) | |
|---|---|
| 3075 | (H—C=C) |
| 2950 | (C—H) |
| 1625 | (C=C) |
| 1250, 800 | (Si—(CH$_3$)$_2$) |
| 1060 | (Si—O) |

Elemental analysis: as C$_{12}$H$_{22}$OSi$_2$

| | C (%) | H (%) |
|---|---|---|
| Calcd. | 60.44 | 9.30 |
| Found | 60.53 | 9.35 |

EXAMPLE 2

Substantially the same flask as used in Example 1 was charged with 330 ml of a tetrahydrofuran solution of 1,3-butadien-2-yl magnesium chloride (660 mmol) under a stream of nitrogen. The contents of the flask was cooled to 0° C., and 66.8 g (330 mmol) of 1,1,3,3-tetramethyl-1,3-dichlorodisiloxane was added dropwise thereto, followed by aging for 2 hours at a temperature of 25° C.

After the aging was over, the reaction mixture was treated in the same manner as in Example 1, to give 47.1 g of the objective compound (yield: 60%).

The compound thus obtained was analyzed in the same manner as in Example 1 and, as a result, was identified as 1,1,3,3-tetramethyl-1,3-bis[2-(1,3-butadienyl)-]disiloxane.

EXAMPLE 3

A 1-liter flask equipped with a reflux condenser, a thermometer, a stirrer and a dropping funnel was charged with 400 ml of an aqueous solution containing 100.8 g (1.8 mol) of potassium hydroxide. While the contents of the flask was maintained at 25° C., 200 ml of a methylene chloride solution of 92.4 g (0.6 mol) of 2-(methylvinylmethoxysilyl)-1,3-butadiene was added dropwise thereto. After the dropwise addition was over, the reaction mixture was aged with stirring at 25° C. for 10 hours. After the reaction is over, 300 ml of n-hexane was added to the reaction mixture, and the resulting organic layer was washed two times with 100 ml each of water. The organic layer thus obtained was distilled, to give 40.9 g of the objective compound (yield: 52%).

The compound thus obtained was subjected to measurement of $^1$HNMR, mass spectrum, IR absorption spectrum and elemental analysis. The results are shown below. It was confirmed by the measurement results that the compound is 1,3-dimethyl-1,3-divinyl-1,3-bis[2-(1,3-butadienyl)]disiloxane.

$^1$HNMR: CCl$_4$
δ (ppm)
0.41 (S, 6H, SiC$\underline{H}_3$)

5.07 (d, J = 10 Hz, 2H, 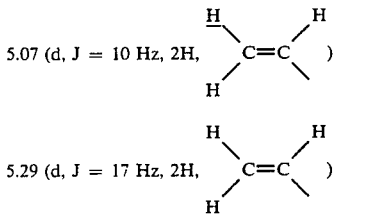 )

5.29 (d, J = 17 Hz, 2H, 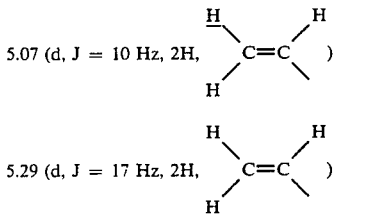 )

5.61, 5.81 (2d, J = 3 Hz, 4H, C$\underline{H}_2$=C)
5.59–6.32 (m, 6H, Si—C$\underline{H}$=C$\underline{H}_2$)
6.38 (dd, J = 10, 17 Hz, 2H, C—C$\underline{H}$=CH$_2$)
Mass spectrum:
262 (M$^+$), 247 (M$^+$ —CH$_3$)
IR absorption spectrum: shown in FIG. 2.

| (cm$^{-1}$) | |
|---|---|
| 3075 | (H—C=C) |
| 2950 | (C—H) |
| 1625 | (C=C) |
| 1260, 800 | (Si—CH$_3$) |
| 1060 | (Si—O) |

Elemental analysis: as C$_{14}$H$_{22}$OSi$_2$

| | C (%) | H (%) |
|---|---|---|
| Calcd. | 64.06 | 8.45 |
| Found | 64.11 | 8.48 |

EXAMPLE 4

Substantially the same flask as used in Example 1 was charged with 450 ml of an aqueous solution of 112.0 g (2.0 mol) of potassium hydroxide. The contents of the flask was cooled to 5° C., and 300 ml of a chloroform solution containing 154.0 g (1.0 mol) of 1-(methylvinylmethoxysilyl)-1,3-butadiene was added dropwise thereto. After the dropwise addition was over, the reaction mixture was aged with stirring at 5° C. for 20 hours. Thereafter, the reaction mixture was treated in the same manner as in Example 1, to give 46 g of the objective compound (yield: 35%). The compound thus obtained was analyzed in the same manner as in Example 1 and, as a result, was identified as 1,3-dimethyl-1,3-divinyl-1,3-bis[2-(1,3-butadienyl)]disiloxane.

We claim:

1. A butadienyl group-containing siloxane compound having the following formula [1]:

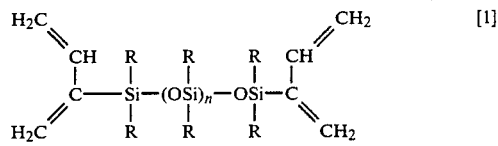

wherein each R is a substituted or unsubstituted monovalent hydrocarbon group having from 1 to 10 carbon atoms, the R groups may be the same or different, and n is an integer of from 0 to 100.

2. The siloxane compound according to claim 1, wherein the R groups in the formula [1] are each a C$_1$–C$_4$ alkyl group, a C$_1$–C$_4$ alkenyl group, a C$_6$–C$_{15}$ aryl group or a corresponding substituted hydrocarbon group derived from the above hydrocarbon groups by substitution of halogen atoms for some or all of the hydrogen atoms in the groups.

3. The siloxane compound according to claim 1, having the following formula [2]:

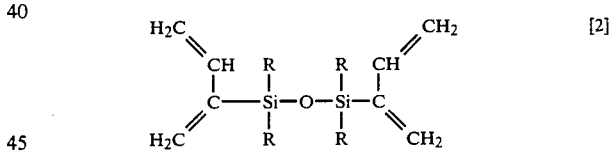

wherein each R is independently a methyl or vinyl group.

4. The siloxane compound according to claim 3, which is 1,1,3,3-tetramethyl-1,3-bis[2-(1,3-butadienyl)-]disiloxane, 1,3-dimethyl-1,3-divinyl-1,3-bis[ 2-(1,3-butadienyl)]disiloxane or 1,1,3,3-tetravinyl-1,3-bis[2-(1,3-butadienyl)]disiloxane.

5. A method of producing the butadienyl group-containing siloxane compound as defined in claim 1, which method comprises reacting:

(a) a 1,3-butadien-2-yl magnesium halide having the following formula [3]:

wherein X$^1$ is a halogen atom, with (b) a siloxane compound having the following formula [4]:

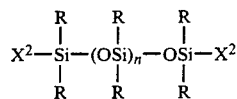

wherein $X^2$ is a halogen atom or an alkoxy group, the two $X^2$ groups may be the same or different from each other, and R and n are as defined above.

6. The method according to claim 5, wherein the reaction is carried out at a temperature of from $-50$ to $100°$ C.

7. The method according to claim 5, wherein the ratio of the amount of the 1,3-butadien-2-yl magnesium halide having the formula [3] to the amount of the siloxane compound having the formula [4] is in the range from 1:0.1 to 1:2, on the molar basis.

8. A method of producing a butadienyl group-containing siloxane compound having the general formula [2]:

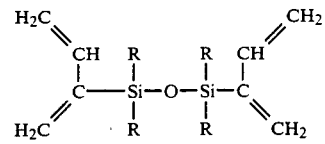

wherein R is as defined above, the method comprising the step of subjecting a butadienyl group-containing silane compound having the formula [5]:

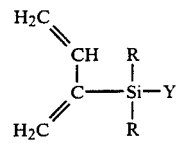

wherein Y is a hydrolyzable atom or group, and R is as defined above, to hydrolysis, followed by condensation reaction.

9. The method according to claim 8, wherein the reaction is carried out at a temperature of from $0°$ to $100°$ C.

10. The method according to claim 8, wherein the hydrolysis is carried out by use of an aqueous solution of an alkali compound, and the ratio of the amount of the silane compound having the formula [5] to the amount of the alkali compound is in the range from 1:0.5 to 1:10, on the molar basis.

* * * * *